United States Patent [19]
Yokoyama et al.

[11] Patent Number: 5,827,712
[45] Date of Patent: Oct. 27, 1998

[54] PROCESS FOR EFFICIENTLY PRODUCING TRANSGLUTAMINASE THROUGH DNA RECOMBINATION

[75] Inventors: Keiichi Yokoyama; Yoshimi Kikuchi; Hisashi Yasueda, all of Kawasaki, Japan

[73] Assignee: Ajinomoto Co., Inc., Tokyo, Japan

[21] Appl. No.: 649,193

[22] Filed: May 17, 1996

[30] Foreign Application Priority Data

May 17, 1995 [JP] Japan ..................................... 7-118067

[51] Int. Cl.⁶ .............................. C12N 9/10; C12P 21/06; C07K 1/00; C07H 21/04
[52] U.S. Cl. ................... 435/193; 435/69.1; 435/252.33; 435/320.1; 530/350; 530/825; 536/23.2; 536/23.7
[58] Field of Search .............................. 435/69.1, 252.33, 435/193, 320.1; 536/23.2, 23.7; 530/350, 825

[56] References Cited

U.S. PATENT DOCUMENTS

| | | | |
|---|---|---|---|
| 5,420,025 | 5/1995 | Takagi et al. | 435/193 |
| 5,514,573 | 5/1996 | Yasueda et al. | 435/193 |

FOREIGN PATENT DOCUMENTS

| | | | |
|---|---|---|---|
| 0 555 649 | 8/1983 | European Pat. Off. | |
| WO 93/25681 | 12/1993 | WIPO | |
| WO 94/23042 | 10/1994 | WIPO | |

OTHER PUBLICATIONS

Yasushi Kawata, et al., FEBS Letters, vol. 345, No. 2/03, pp. 229–232, "Chaperonin Groe and ADP Facilitate the Folding of Various Proteins and Protect Against Heat Inactivation", May 30, 1994.

Thomas Langer, et al., Nature, vol. 356, pp. 683–689, "Successive Action of DNAK, DNAJ, and Groel Along the Pathway of Chaperone–Mediated Protein Folding", Apr. 23, 1992.

Koji Ikura, et al., European Journal of Biochemistry, vol. 187, pp. 705–711, "Expression of Guinea–Pig Liver Transglutaminase CDNA in *Escherichia Coli*", 1990.

Ohki et al. (1986) J. Biol. Chem. 261, 1778–1781.

Lee et al. (1992) J. Biol. Chem. 267, 2849–2852.

*Primary Examiner*—Eric Grimes
*Assistant Examiner*—Elizabeth Slobodyansky
*Attorney, Agent, or Firm*—Oblon, Spivak, McClelland, Maier & Neustadt, P.C.

[57] ABSTRACT

The present invention relates to a process for producing a transglutaminase, which comprises incubating *Escherichia coli* expressing genes encoding a heat shock protein (DnaJ) and a transglutaminase. The transglutaminase is produced in large quantities, at low cost and has the appropriate stereostructure to render the transglutaminase biologically active. The transglutaminase so produced is useful in the food industry.

25 Claims, 1 Drawing Sheet

PROCESS FOR EFFICIENTLY PRODUCING TRANSGLUTAMINASE THROUGH DNA RECOMBINATION

FIELD OF THE INVENTION

The present invention relates to a process for efficiently producing a desired transglutaminase (hereinafter abbreviated as "TG") by incubating E. coli transformed with DNA encoding said TG. More specifically, the present invention relates to a process for producing TG in which E. coli over-expresses TG in soluble form, such that its biological activity is maintained.

DISCUSSION OF THE BACKGROUND

Methods for producing a desired polypeptide in cells by transforming E. coli with recombinant DNA are presently widely used. However, when the E. coli over-expresses the desired polypeptide by this method, the polypeptide accumulates in a denatured state lacking the inherent higher-order structure of the active polypeptide. Generally, the polypeptide accumulates in insoluble granules which are called inclusion bodies [Schein, Bio/Technology, 7: 1141–1149 (1989)].

In order to isolate the biologically active polypeptide from the insoluble granules, a series of intricate procedures are generally required, in which the granules are treated in a denaturation solution using a denaturant such as guanidine hydrochloride or urea, the polypeptides are released from the granules, and the stereostructure is regenerated using the appropriate treatment [Kohno et al., Methods in Enzymology, vol. 198, pp. 187].

The following methods are known for regenerating the stereostructure:

(1) a method in which a denaturant is gradually removed from a denaturation solution containing a desired polypeptide; and (2) a method in which a desired polypeptide having an intramolecular disulfide bond is incubated in a redox-type denaturant containing oxidative and reductive glutathiones in suitable amounts.

However, the regeneration efficiency of these methods is extremely low. Moreover, using these methods, the stereostructure of some proteins cannot be completely regenerated in-vitro. Thus, it is difficult to obtain a desired polypeptide with biological activity and the correct stereostructure using E. coli as a host. In addition, it is costly and laborious to conduct the purification required to obtain the desired polypeptide. Furthermore, when the recombinant polypeptide is administered for therapy, a polypeptide which has not been completely regenerated exhibits antigenicity in-vivo, posing quite a serious problem.

Various techniques have been developed to solve the above-mentioned problem associated with the formation of the insoluble granules. It is known that decreasing the temperature at which microorganisms (especially E. coli) are incubated improves production of the desired polypeptide [Schein, et al., Bio/Technology, 6, 291–294 (1988), and Kopetzki et al., Mol. Gen. Genet., 216, 149–155 (1989)]. However, this low-temperature incubation is associated with problems due to the decreased growth rate of E. coli as a host, resulting in a decreased amount of the desired polypeptide being produced.

Alternatively, it has been reported that the stereostructure of the desired polypeptide may be generated after secretion from E. coli. However, in general, E. coli does not productively secrete foreign polypeptides, and when the desired polypeptide is inherently a non-secretory polypeptide, the production of the desired polypeptide is even further decreased.

Recently, a group of heat shock proteins has been identified which are called molecular chaperons, which assist in the formation of regeneration of protein stereostructure in-vitro [Gething et al., Nature, vol. 355, p. 33 (1992)]. It is believed that when the stereostructures of proteins have collapsed, these molecular chaperons temporarily stabilize these proteins to prevent inappropriate denaturation. DnaK, GroEL and GroES are examples of such chaperons present in E. coli.

Thus, having identified co-factors (molecular chaperons) that assist in the regeneration of the stereostructure of proteins, the effect of excessive expression of the molecular chaperon on the suppression of insolubilization of the desired polypeptide was studied. Lee et al. successfully improved the solubility of a desired polypeptide, procollagen, by over-expressing either DnaK alone or GroEL and GroES (Lee et al., J. Biol. Chem. 267: 2849–2852 (1992)].

Recently, Gaspers et al. reported that during the expression of protein tyrosine kinase in E. coli, (1) GroEL and GroES; or (2) all of DnaK, DnaJ and GrpE are simultaneously transduced in the host, resulting in an increased amount of soluble kinase [Gaspers et al., Cell. Mol. Biol., 40: 635–644 (1994)]. However, it was unclear whether the kinase exhibited biological activity. It was further reported that the total amount of the expressed kinase was decreased. Generally, there is a correlation between a decreased rate of synthesis of a protein and an increased solubility of the polypeptide [Kopetzki et al., Mol. Gen., Genet., vol. 216, pp. 149–155 (1989)]. Thus, it was unclear from this report whether the effect seen was a result of the activity of the molecular chaperon or a result of the decreased production of the molecular chaperon by the E. coli host. Thus, this report did not elucidate the mechanism which was responsible for this effect TG is an enzyme that catalyzes a transfer reaction of an acyl group of a γ-carboxyamide group of a glutamine residue in a peptide chain. When TG reacts with an ε-amino group of a lysine residue in a protein, an ε(γ-glutamyl)lysine crosslink is formed either intramolecularly or intermolecularly. When a primary amine such as an amino acid, amino acid derivative or the like is present as an acyl acceptor, it is transduced into the protein. When water acts as the acyl acceptor, TG catalyzes the reaction of deamidating a glutamine residue into a glutamic acid residue.

TG has been used in producing gel-like food, gel-like toiletries, yogurt, jelly, cheese and the like [Japanese Patent Publication No. 50,382/1989 and Japanese Laid-Open Patent Application (Kokai) No. 27,471/1989]. TG is an enzyme which is found in various tissues and organs of mammals, plants, fish eggs and microorganisms. TG has been isolated from guinea pig [Connellan et al., Journal of Biological Chemistry, vol. 246, No. 4, pp. 1093–1098 (1971)], and microorganisms [see Japanese Laid-Open Patent Application (Kokai) No. 27,471/1989]. Human blood coagulation factor XIII has also been identified as a TG [Takahashi et al., Proc. Natl. Acad. Sci., U.S.A., vol. 83, pp. 8019–8023 (1986)].

Further, the present inventors have recently purified TG from fish, have obtained the gene and the cDNA, and have clarified the structure thereof [Japanese Laid-Open Patent Application (Kokai) No. 23,787/1995].

TG derived from guinea pig liver [Ikura et al., Eur. J. Biochem., vol. 187, pp. 705–711 (1990)] and the TG of human blood coagulation factor XIII [Board et al., Thrombosis and Haemostasis, vol. 63, No. 2, pp. 235–240 (1990)] have been produced recombinantly using E. coli as a host. However, in both cases, the amount of the enzyme as detected by antibody binding thereto is quite small.

SUMMARY OF THE INVENTION

In view of the aforementioned deficiencies attendant with prior art methods for producing recombinant proteins using E. coli as a host, it is evident that there exists a need in the art for a method for producing in E. coli a soluble polypeptide having biological activity.

The present inventors successfully produced large quantities of TG derived from a red sea bream recombinant DNA using E. coli as a host. The successful production of TG in E. coli was unexpected, (Japanese Laid-open Patent Application (Kokai) No. 225,775/1994] because when E. coli expressing recombinant TG was incubated at 37° C., the TG produced formed inclusion bodies in the cell. Thus, TG accumulated as an inactive substance. In contrast, TG exhibiting biological activity was produced at an incubation temperature of 30° C. However, a detailed analysis of the accumulated TG demonstrated that insoluble TG, not recovered in the cell extract of E. coli, is approximately 4/5 of the total TG produced. Thus, even at an incubation temperature of 30° C., the majority of the TG did not accumulate in a sufficiently soluble state.

Moreover, when cells producing TG were incubated at a low incubation temperature, although the ratio of soluble to insoluble molecules of TG increased, the total amount of TG produced significantly decreased. Therefore, conventional methods could not use E. coli as a host to efficiently produce large quantities of the desired TG polypeptide.

In view of the industrial applicability of fish TG for food processing, a process for producing TG in large amounts at low cost has been required. To achieve this goal, the present inventors used techniques to inhibit or suppress the insolubilization, i.e., to increase the solubility, of the desired polypeptide which is mass-produced in productive host cells. For the mass-production of TG, the present inventors have discovered a method in which insoluble TG in cells is solubilized, and large amounts of TG having a stereostructure providing biological activity accumulates.

The present inventors first investigated the ability of GroEL, GroES and DnaK to solubilize a desired TG polypeptide. However, results with these chaperons demonstrated that these gene products, were not sufficient to suppress the insolubilization, and moreover, appeared to inhibit the growth of the host cells.

Accordingly, the present inventors have surprisingly found that DnaJ, unlike the conventional co-factor chaperons GroEL, GroES and DnaK, is effective for solubilizing and accumulating the desired TG polypeptide in cells, in large quantities and in a biologically active state. By "biologically active" is meant that the TG polypeptide exhibits transglutaminase activity. It has been found through further analysis that this DnaJ plays a central role in the solubilization of TG, and that the effects of solubilization and accumulation in a biologically active state are stabilized upon the addition of the dnaK gene products.

Thus, it has been surprisingly found that a desired polypeptide may be produced in large quantities and in a biologically active state using E. coli which over-expresses DnaJ or DnaJ and DnaK as a host. This finding has led to the successful development of a process for producing the desired TG polypeptide efficiently and economically, which is central to the present invention.

The present invention can be applied to TG from any source, however TG derived from fish is preferred. The TG produced by the present invention is particularly useful in the food industry because the enzyme is produced in large quantities and at a low cost.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
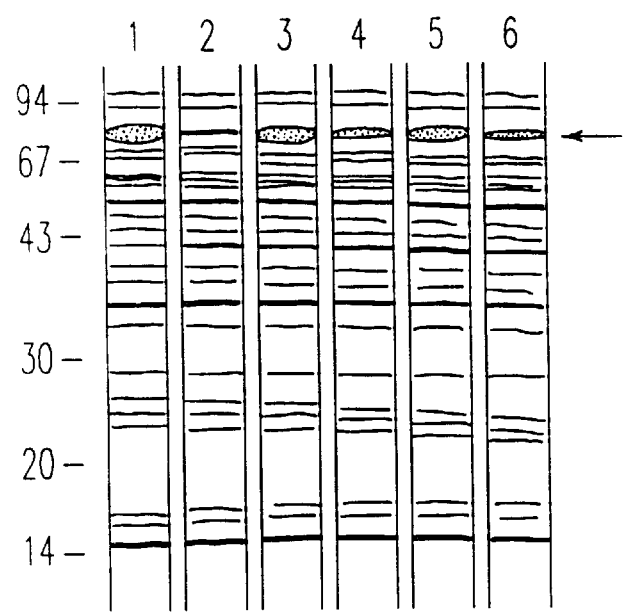
FIG. 1 is a view showing the results of analysis through SDS-PAGE.

Row 1 is all of fractions of E. coli strain HB101 containing pTTG2-22 and pSTV28.

Row 2 is centrifuged supernatant fractions of E. coli strain HB101 containing pTTG2-22 and pSTV28.

Row 3 is all of fractions of E. coli strain HB101 containing pTTG2-22 and pDnaj-01 (AJ13097, FERM P-14913; FERM BP-5438).

Row 4 is centrifuged supernatant fractions of E. coli strain HB101 containing pTTG2-22 and pDnaJ01 (AJ13097, FERM P-14913; FERM BP-5438).

Row 5 is all of fractions of E. coli strain HB101 containing pTTG2-22 and pDnaKJ-01 (AJ13096, FERM P-14912; FERM BP-5437).

Row 6 is centrifuged supernatant fractions of E. coli strain HB101 containing pTTG2-22 and pDnaKJ01 (AJ13096, FERM P-14912; FERM BP-5437).

The figures on the left side indicate molecular weights (×1000) of protein markers subjected to electrophoresis at the same time.

The arrow (→) on the right side indicates a molecular weight of TG derived from a red sea bream.

DESCRIPTION OF THE PREFERRED EMBODIMENTS DETAILED DESCRIPTION

The present invention relates to, as mentioned above, a process for producing TG using as a host E. coli in which the expression of (1) a dnaJ gene or (2) a dnaK gene and a dnaJ gene is enhanced. In a preferred embodiment, the present invention relates to a process for producing TG, which comprises incubating E. coli that contains (1) a vector containing (a) a dnaJ gene or (b) a dnaJ gene and a dnaK gene; and (2) a vector that contains a gene encoding a desired TG polypeptide, and collecting the desired TG which accumulates in the cells in a biologically active state.

DnaK is one of the main heat shock proteins of E. coli, and is synthesized correspondingly in response to heat and other various environmental stresses. Thus, this gene product plays a significant role in the formation of protein stereostructure in cells.

DnaJ is known as a factor that complements the reaction of DnaK [Gething et al., Nature, vol. 355, pp. 33–45 (1992)].

Examples of methods for obtaining these chaperon genes include: (1) a method in which conventional cloning methods are used to clone a gene that complements the temperature sensitivity of these temperature sensitive strains, from a chromosome of a wild-type strain of E. coli, and (2) cloning using the polymerase chain reaction (PCR), because DNA sequences of these chaperons are known.

The expression of (1) the dnaJ gene or (2) the dnaK and dnaJ genes and/or TG gene may be conducted using the natural promoters thereof, promoters conventionally used in vectors, or various promoters derived from *E. coli*. Examples include trp promoter and lac promoter. The vectors in which to insert (1) the dnaJ gene or (2) the dnaK and dnaJ genes and/or TG gene may be derived from commercial sources or may be specially produced. Any vector may be used, including a plasmid vector, a phage vector, a transposon vector, and the like. Since the plasmid for mass-production of the desired TG polypeptide is a pBR322, pUC18 or pUC19 derivative in most cases, a plasmid vector which can co-exist with these plasmids is preferably used. Accordingly, a plasmid vector such as pACYC184 and pMW118 is preferably used. The two vectors, namely, the vector containing the gene encoding the heat shock protein DnaJ and the vector containing the gene encoding TG may be co-transformed into *E. coli*.

Alternatively, the expression system of (1) the dnaJ gene or (2) the dnaK and dnaJ genes may be integrated into the expression plasmid encoding the desired TG polypeptide. Thus, a vector for the expression of both the gene encoding DnaJ and the gene encoding TG may be used.

Another alternative host for producing the desired TG polypeptide is a strain in which the expression of (1) the dnaJ gene or (2) the dnaJ and dnaK genes present on the chromosome of the host *E. coli* is enhanced, i.e., a strain which over-expresses the dnaJ and/or dnaK gene products.

The expression of the chaperons may be enhanced by a preparing in vitro a chaperon expression system wherein a strong promoter such as the lac promoter or the like is placed upstream of the chaperon and this construct is used to replace the chaperon genes in the *E. coli* chromosome. Alternatively, chaperon expression may be increased by increasing the number of chaperon genes on the chromosome.

The plasmid for expressing TG may be obtained by the method described in Japanese Laid-Open Patent Application (Kokai) No. 225,775/1994 (see European Laid-Open Application EP-0555649A) which is incorporated herein by reference in its entirety.

The preparation of various transformants containing an expression vector containing the TG gene, or a vector containing heat shock protein genes, such as dnaJ, dnaK and the like, are described below.

The microorganism to be used as a transformant in the present invention is *E. coli* strain K-12. *E. coli* strain HB101 or JM109 is preferable. These transformants expressing TG isolated from red sea bream are incubated in a suitable culture medium, whereby the TG is produced and accumulates in cells.

The transformation is conducted by conventional methods including the calcium chloride method, electroporation, DEAE dextran, lipofection or the like. These and other methods are described in Sambrook et al., Molecular Cloning, Laboratory Manual, Cold Spring Harbor Laboratory Press, New York (1989).

The conditions for incubation can be appropriately selected by those skilled in the art, according to the type of transformant or type of gene expression system. The TG which has been expressed and accumulates in the cells can be isolated and purified by known methods. For example, the recombinant TG can be purified by the method reported in Yasueda et al., Biosci. Biotech. Biochem., 58, 2041–2045 (1994), which is incorporated herein by reference in its entirety.

The activity of TG is determined by conducting a reaction using dimethylated casein and monodansyl cadaverine as substrates and measuring the increase in the fluorescence intensity of casein, which fluorescence is derived from monodansyl cadaverine. The composition of the reaction solution is described below.

<Composition of a reaction solution>

1.0 mg/ml dimethylated casein 0.015 mM monodansyl cadaverine 3.0 mM dithiothreitol 50 mM tris-hydrochloride buffer (pH 7.5)

5 mM calcium chloride

The above-mentioned conditions are employed in the following Examples unless otherwise instructed.

To 2.4 ml of the reaction solution are added from 20 to 100 μl of a TG solution, and the mixture is reacted at 37° C. for 30 minutes. Then, 100 μl of 500-mM EDTA are added thereto to stop the reaction, and the fluorescence intensity is measured by means of RF-1500 (manufactured by Shimadzu Corporation, excitation wave length 350 nm, fluorescence wave length 480 nm).

The present invention will be illustrated in more detail by referring to the following Examples. However, the present invention is not limited to these Examples.

EXAMPLES

Having generally described this invention, a further understanding can be obtained by reference to certain specific examples which are provided herein for purposes of illustration only and are not intended to be limiting unless otherwise specified.

Example 1

Process for producing a transglutaminase of a red sea bream:

(1) Cloning of a group of dnak, dnaJ and groESL genes encoding heat shock proteins The present inventors cloned the genes for the heat shock proteins from a chromosome of *E. coli* through PCR (Erlich et al., Nature, vol. 331, pp. 461–462 (1988), incorporated herein by reference in its entirety].

The base sequences of the genes, dnaK (Cowing et al., Proc. Natl. Acad. Sci. U.S.A. , vol. 82, pp. 2679–2683 (1985), Bardwell et al., Proc. Natl. Acad. Sci. U.S.A., vol. 81, pp. 848–852 (1984)], dnaJ [Ohki et al., J. Biol. Chem., vol. 261, pp. 1778–1781 (1986)] and groESL [Hemmingsen et al., Nature, vol. 333, pp. 330–334 (1988)] are known. Two types of DNA primers were prepared. First, primers DNAK-01 (5'-CCTTGATGACGTGGTTTACG-3') (SEQ ID NO: 1) and DNAK-02 (5'-CCTTCGCCCGTGTCAGTATA-3') (SEQ ID NO: 2) were prepared for dnaK; primers DNAJ-01 (5'CTGATGGAATTCGCCCAGCA-3') (SEQ ID NO: 3) and DNAJ-02 (5° CGTGAGAGGAATTCATCGGC-3') (SEQ ID NO: 4) were prepared for dnaJ; and GROELS-01 (5'-GACGTCGATAGCAGGCCAAT-3') (SEQ ID NO: 5) and GROESL-02 (5'-GACGCACTCGCGTCGTCCGT-3') (SEQ ID NO: 6) were prepared for groESL. Restriction endonuclease EcoRI cleavage recognition sequences were integrated into the 5'-terminals of the DNA fragments of the primers DNAJ-01 and DNAJ-02.

A three-part PCR reaction was used, namely at 94° C. for 1 minute, at 37° C. for 2 minutes and at 72° C. for 3 minutes. This reaction was repeated for a total of 25 times using *E*.

coli genomic DNA as a template and the respective DNA primers to conduct the amplification. As a result, the DNA fragments of the desired genes, dnaK, dnaJ and groESL were amplified and obtained.

For the dnaK gene, the terminals of the amplified DNA fragment were blunt-ended, and then inserted into a HincII site of the commercial plasmid vector pSTV28 (made by Takara Shuzo) to construct plasmid pDnaK-01. Because the replication origin of this plasmid is p15A, this plasmid can co-exist with plasmid pBR322 or pUC19 derivatives in one cell.

For the groESL gene, the DNA fragment amplified through PCR was inserted into a HincII site of the commercial vector pSTV28 to construct pGroESL-01.

For the dnaJ gene, the DNA fragment amplified through PCR was first treated with EcoRI and then inserted into an EcoRI site of the commercial cloning vector pSTV28 to construct DnaJ expression plasmid pDnaJ-01.

(2) Cloning of the operon of heat shock protein DnaK and DnaJ genes.

The base sequences of the operon of dnaK and dnaJ genes are known [Cowing et al., Proc. Natl. Acad. Sci. USA, vol 82, pp. 2679–2683 (1985), Bardwell et al, Proc. Natl. Acad. Sci., USA, vol. 81, pp. 848–852 (1984), and Ohki et al., J. Biol. Chem., vol. 261, pp. 1778–1781 (1986)]. Therefore, the desired gene group was likewise cloned through PCR. The primers used were primer DNAKJ-01: 5'-CCTGGA-TCCCGTGGTTTACGACCCCATTTAGTAGTC-3' (SEQ ID NO: 7) and primer DNAKJ-02: 5'-TTCACCTGC-AGGTTAAATCATATCAGGCGTAATAC-3' (SEQ ID NO: 8). The cleavage recognition sites for BamHI and Sse8387I were integrated into the 5'-terminals of the primers DNAKJ-01 and DNAKJ-02, respectively. The template DNA for amplification was a genome produced from E. coli strain HB101. When PCR was conducted, a DNA fragment of approximately 3.4 kbp corresponding to the desired gene operon fragment was obtained. With respect to the PCR conditions, after the completion of the heat denaturation at 94° C. for 90 seconds, a two-part reaction, namely at 98° C. for 10 seconds and at 68° C. for 5.5 minutes was repeated for a total of 25 times, and a reaction at 72° C. for 10 minutes was then conducted.

The thus-obtained DNA fragment was treated with BamHI and Sse8387I to obtain a PCR-amplified fragment having the respective restriction endonuclease cleavage terminals. pSTV28 was used as a vector. This vector was treated with the same restriction endonucleases, and the above-obtained PCR-amplified DNA fragment was cloned therein to construct plasmid pDnaKJ-01.

(3) Production of TG of a red sea bream in an E. coli in which a heat shock protein is over-expressed:

Plasmid pTTG2-22 that expresses TG from red sea bream at a high level [E. coli strain HB101 (AJ12742) containing this plasmid was listed as deposited at the National Institute of Bioscience and Human Technology (hereinafter referred to as "NIBHT") of the Agency of Industrial Science and Technology under deposit No. FERM BP4117] is described in Japanese Laid-Open Patent Application (Kokai) No. 225,775/1994 and European Patent Laid-Open No. EP-0555639A, which is incorporated herein by reference in its entirety.

The above-mentioned chaperon gene expression plasmids were transformed into E. coli by a known method using this TG producing strain.

Escherichia coli AJ13096 was deposited on May 1, 1995 at National Institute of Bioscience and Human-Technology Agency of Industrial Science and Technology and given a domestic deposition number, FERM P-14912. On Mar. 4, 1996, Escherichia coli AJ13096 was transferred into the international deposition phase and given an international deposition number, FERM BP-5437.

Escherichia coli AJ13097 was deposited on May 1, 1995 at National Institute of Bioscience and Human-Technology Agency of Industrial Science and Technology and given a domestic deposition number, FERM P-14913. On Mar. 4, 1996, Escherichia coli AJ13097 was transferred into the international deposition phase and given an international deposition number, FERM BP-5438.

Escherichia coli AJ13098 was deposited on May 1, 1995 at National Institute of Bioscience and Human-Technology Agency of Industrial Science and Technology and given a domestic deposition number, FERM P-14914. On Mar. 4, 1996, Escherichia coli AJ13098 was transferred into the international deposition phase and given an international deposition number, FERM BP-5439.

Escherichia coli AJ13099 was deposited on May 1, 1995 at National Institute of Bioscience and Human-Technology Agency of Industrial Science and Technology and given a domestic deposition number, FERM P-14915. On Mar. 4, 1996, Escherichia coli AJ13099 was transferred into the international deposition phase and given an international deposition number, FERM BP-5440.

Colonies of each of the thus-obtained transformants were inoculated in 3 ml of a 2×TY medium (composition: 1.6-% bactotryptone, 1% yeast extract and 0.5% NaCl, pH 7) containing 100 μg/ml of ampicillin and 30 μg/ml of chloramphenicol, and were incubated at 32° C. for 14 hours while being shaken.

Then, 0.5 ml of the above-obtained culture solution was inoculated in a Sakaguchi flask filled with M-9 modified casamino acid medium (containing 15.1 g of sodium dihydrogenphosphate 12-hydrate, 3.0 g of potassium dihydrogenphosphate, 8.0 g of casamino acid, 0.2 g of yeast extract, 0.2 g of L-leucine, 0.2 g of L-proline, 2 mg of vitamin B1 hydrochloride, 0.5 g of magnesium sulfate, 14.5 mg of calcium chloride 2-hydrate and 5.0 g of glucose in 1 liter of a medium). The mixture was incubated at 28° C., 32° C. and 37° C. for 20 hours while being shaken, and the cells were collected through centrifugation.

The thus-collected cells were suspended in 30 ml of a milled cell solution [containing 20 mM Tris-HCl (pH 7.5), 30 mM NaCl and 5 mM EDTA). Further, 10 mg/ml of a lysozyme solution was further added in an amount of 2 ml, and the resulting mixture was allowed to stand on ice for 2 hours. Subsequently, the cell suspension was sonicated, and then centrifuged at 20,000×g for 10 minutes to prepare a sonicated cell supernatant.

E. coli containing pTTG2-22 and vector pSTV28 as a control were also sonicated, and then centrifuged to obtain a sonicated cell supernatant.

The proteins contained in all of the fractions of the sonicated cell solutions obtained by incubating (1) E. coli strain AJ13096 (FERM P-14912; FERM BP-5437), (2) E. coli strain AJ13097 (FERM P-14913; FERM BP-5438) and (3) E. coli strain HB101 containing pTTG2-22 and pSTV28 at 32° C. and of the supernatant fractions obtained by centrifugation were analyzed on SDS-PAGE (polyacrylamide gel electrophoresis), and the results are shown in FIG. 1.

As is apparent from the results, no TG protein was observed in the centrifuged supernatant fraction of E. coli strain HB101 containing pTTG2-22 and pSTV28.

Then, the centrifuged supernatant fractions of (1) *E. coli* strain HB101 containing pTTG2-22 and pSTV28, (2) *E. coli* strain AJ13098 containing pTTG2-22 and pDnaK-01 (FERM P-14914; FERM BP-5439), (3) *E. coli* strain AJ13099 strain containing pTTG2-22 and pGroESL-01 (FERM P-14915; FERM BP-5440), (4) *E. coli* strain AJ13097 containing pTTG2-22, pTTG2-22 and pDnaJ-01 (FERM P-14913; FERM BP-5438) and (5) *E. coli* strain AJ13096 containing pTTG2-22, pDnaKJ-01 (FERM P-14912; FERM BP-5437) were measured for TG activity. The results are shown in Table 1.

*E. coli* AJ13096, AJ13097, AJ13098 and AJ13099 were deposited on May 1, 1995 at the National Institute of Bioscience and Human Technology Agency of Industrial Science and Technology as deposit numbers FERM P-14912, FERM P-14913, FERM P-14914 and FERM P-14915, respectively, and were transferred into the international phases on Mar. 4, 1996 as deposit numbers FERM BP-5437, FERM BP-5438, FERM BP-5439, and FERM BP-5440, respectively.

TABLE 1

| Plasmid contained in *E. coli* | Increased value of fluorescence intensity/incubation temperature (final OD) | | |
|---|---|---|---|
| pTTG 2-22, pSTV28 | 42.1/28° C. (4.3) | 18.5/32° C. (5.0) | 1.3/37° C. (5,9) |
| pTTG2-22, pDnaK-01 | 31.8/28° C. (4.1) | 11.8/32° C. (4.2) | 9.7/37° C. (4.6) |
| pTTG2-22, pGroESL-01 | 34.8/28° C. (5.0) | 26.1/32° C. (3.8) | N.D. |
| pTTG2-22, pDnaJ-01 | 58.5/28° C. (5.2) | 57.2/32° C. (5.2) | 1.3/37° C. (5.8) |
| pTTG2-22, pDnaKJ-01 | 52.5/28° C. (4.4) | 82.8/32° C. (5.2) | 1.5/37° C. (5.5) |

As shown in Table 1, it has been found that biologically active transglutaminase is mass-produced in the strain in which DnaJ is over-expressed, and that the effect is stabilized when DnaJ and DnaK co-exist. This result was unexpected in light of the performance of the conventional main chaperons, DnaK and GroESL.

TG has been favored as an enzyme for modifying properties of food proteins. The mass production of this enzyme through recombinant DNA is an effective method, but in the past suffered from the accumulation of mass-produced inactive TG in *E. coli* strains.

However, the present method, using heat shock protein(s), (1) DnaJ or (2) DnaJ and DnaK, can result in the mass-production of the desired TG in a soluble state.

Thus, the method of the present invention is a breakthrough over the conventional method of producing TG. Further, the present invention advantageously obviates the necessity of regenerating the stereostructure of an insoluble desired TG in-vitro.

Therefore, according to the present invention, not only can TG be produced in quite large quantities, but also TG can be used more widely industrially.

This application is based on JP 118067/1995, filed May 17, 1995, which is incorporated herein by reference in its entirety.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A process for producing a transglutaminase, which comprises incubating E. coli comprising a gene encoding a heat shock protein DnaJ and a gene encoding a transglutaminase, wherein each of said genes is operably linked in proper reading frame to sequences which direct the expression of each gene such that expression of the DnaJ gene is enhanced and the transglutaminase produced is biologically active and is present in soluble form at a level higher than that of transglutaminase expressed in E. coli in which expression of the DnaJ gene is not enhanced, and collecting the transglutaminase from said E. coli.

2. The process for producing a transglutaminase according to claim 1, wherein said E. coli is transformed with a vector comprising the DnaJ and transglutaminase genes operably linked in proper reading frame to sequences which direct the expression of said genes.

3. The process for producing a transglutaminase according to claim 1, wherein the strain of E. coli is a strain which over-expresses an endogenous gene encoding a heat shock protein DnaJ.

4. The process for producing a transglutaminase according to claim 3, wherein the E. coli is transformed with a vector comprising a gene encoding the transglutaminase, wherein said gene is operably linked in proper reading frame to sequences which direct the expression of said gene encoding the transglutaminase.

5. The process of claim 1, wherein the transglutaminase is a transglutaminase derived from fish.

6. The process of claim 5, herein the transglutaminase is a transglutaminase derived from a red sea bream.

7. The process of claim 1, wherein the E. coli further comprises a gene encoding DnaK.

8. The process for producing a transglutaminase according to claim 7, wherein said E. coli is transformed with a vector comprising the genes encoding the heat shock proteins DnaJ and DnaK and the gene encoding the transglutaminase operably linked in proper reading frame to sequences which direct the expression of said genes, such that the transglutaminase produced is biologically active and is present in soluble form at a level higher than that of transglutaminase expressed in E. coli in the absence of the gene encoding a heat shock protein DnaJ.

9. The process for producing a transglutaminase according to claim 7, wherein the heat shock proteins DnaJ and DnaK are over-expressed.

10. The process for producing a transglutaminase according to claim 9, wherein the strain of E. coli is a strain which over-expresses an endogenous gene encoding a heat shock protein DnaJ.

11. The process for producing a transglutaminase according to claim 10, wherein the E. coli is transformed with a vector comprising a gene encoding the transglutaminase, wherein said gene is operably linked in proper reading frame to sequences which direct the expression of said gene encoding the transglutaminase.

12. The process of claim 11, wherein the transglutaminase is a transglutaminase derived from fish.

13. The process of claim 12, wherein the transglutaminase is a transglutaminase derived from a red sea bream.

14. The process of claim 1, wherein the gene encoding the transglutaminase is present on plasmid pTTG-2.

15. The process of claim 1, wherein the gene encoding the DnaJ is present on plasmid pDnaJ-01.

16. The process of claim 7, wherein the gene encoding the DnaK is present on plasmid pDnaK-01.

17. The process of claim 7, wherein the genes encoding DnaJ and DnaK are present on plasmid pDnaKJ-01.

18. The process of claim 1, wherein the E. coli is AJ-13097, deposited at NIBHT under Deposit No. FERM BP-5438.

19. The process of claim 7, wherein the E. coli is AJ-13096, deposited at NIBHT under Deposit No. FERM BP-5437.

20. An E. coli transformed with sequences encoding a non-E. coli transglutaminase and a heat shock protein DnaJ, wherein expression of said DnaJ is enhanced.

21. The transformed E. coli of claim 20, identified as FERM BP-5438.

22. An E. coli which naturally expresses an enhanced level of DnaJ transformed with sequences encoding a non-E. coli transglutaminase and a heat shock protein DnaK.

23. An E. coli which naturally expresses an enhanced level of DnaJ transformed with sequences encoding a transglutaminase and GroESL.

24. An E. coli transformed with sequences encoding a transglutaminase and heat shock proteins DnaJ and DnaK, wherein expression of DnaJ is enhanced.

25. The transformed E. coli of claim 24, identified as FERM BP-5437.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

C C T T G A T G A C    G T G G T T T A C G    2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCTTCGCCCG TGTCAGTATA                                                                                    20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CTGATGGAAT TCGCCCAGCA                                                                                    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGTGAGAGGA ATTCATCGGC                                                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GACGTCGATA GCAGGCCAAT                                                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GACGCACTCG CGTCGTCCGT                                                                                    20

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCTGGATCCC GTGGTTTACG ACCCCATTTA GTAGTC                                                                   36

(2) INFORMATION FOR SEQ ID NO:8:

( i ) SEQUENCE CHARACTERISTICS:
 ( A ) LENGTH: 35 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:8:

TTCACCTGCA GGTTAAATCA TATCAGGCGT AATAC 35